(12) United States Patent
Al-Olayan et al.

(10) Patent No.: US 11,772,969 B1
(45) Date of Patent: Oct. 3, 2023

(54) SOLAR-POWERED OXYGEN PRODUCTION SYSTEM FOR HOSPITALS

(71) Applicant: KING FAISAL UNIVERSITY, Al-Ahsa (SA)

(72) Inventors: Aisha Al-Olayan, Almubaraz (SA); Hessa Al-Mousa, Almubaraz (SA); Marwah Al-Mutayib, Al-Mubaraz (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/732,464

(22) Filed: Apr. 28, 2022

(51) Int. Cl.
C01B 13/02 (2006.01)
H02S 20/23 (2014.01)
H02J 3/38 (2006.01)
B01D 46/00 (2022.01)
B01J 35/00 (2006.01)
(Continued)

(52) U.S. Cl.
CPC ......... *C01B 13/02* (2013.01); *A61M 16/1005* (2014.02); *B01D 46/0027* (2013.01); *B01J 27/14* (2013.01); *B01J 35/004* (2013.01); *F17C 1/00* (2013.01); *F17D 1/04* (2013.01); *H02J 3/381* (2013.01); *H02S 20/23* (2014.12); *A61M 2205/8206* (2013.01);
(Continued)

(58) Field of Classification Search
None
See application file for complete search history.

(56) References Cited

U.S. PATENT DOCUMENTS

| 4,565,617 A | 1/1986 | Ahuja | |
| 2005/0183962 A1* | 8/2005 | Oakes | C25B 1/04 205/628 |

(Continued)

FOREIGN PATENT DOCUMENTS

| CN | 107754828 B | * 9/2020 | ............... B01J 27/14 |
| CN | 112250058 A | 1/2021 | |
| CN | 112383084 A | 2/2021 | |

OTHER PUBLICATIONS

"Z-Scheme Photocatalytic Water Splitting on a 2D Heterostructure of Black Phosphorus/Bismuth Vanadate Using Visible Light", Angew. Chem. Int. Ed. 2018, 57, p. 2160-2164 (Year: 2018).*

(Continued)

*Primary Examiner* — Lyle Alexander
*Assistant Examiner* — Bryan Kilpatrick
(74) *Attorney, Agent, or Firm* — Nath, Goldberg & Meyer; Richard C. Litman

(57) ABSTRACT

The solar-powered oxygen production system for hospitals is useful for producing oxygen in hospital settings without the need for an external power source. The system includes one or more photovoltaic (PV) solar panels mounted on the roof of a hospital and an oxygen production system housed within the equipment room of the hospital. The solar panels provide the electrical power needed for the oxygen production system. The solar panels are mounted on the roof using solar panel supports. The number of panels and the power output of each panel can be selected depending on the electrical power requirements of the oxygen production system. The oxygen production system includes an LED for activating a black phosphorous catalyst in the atmospheric air to convert water vapor in the air into hydrogen and oxygen.

10 Claims, 4 Drawing Sheets

(51) Int. Cl.
   *B01J 27/14* (2006.01)
   *A61M 16/10* (2006.01)
   *F17D 1/04* (2006.01)
   *F17C 1/00* (2006.01)
   *B01J 19/12* (2006.01)

(52) U.S. Cl.
   CPC . *A61M 2205/8293* (2013.01); *B01D 2279/00* (2013.01); *B01J 19/127* (2013.01); *H02J 2300/24* (2020.01)

(56) References Cited

U.S. PATENT DOCUMENTS

| | | |
|---|---|---|
| 2005/0194041 A1 | 9/2005 | Fan et al. |
| 2009/0178918 A1 | 7/2009 | Gibson et al. |
| 2012/0125780 A1* | 5/2012 | Oakes ............... C25B 1/55 |
| | | 204/266 |
| 2012/0222967 A1* | 9/2012 | Oakes ............... C25B 1/55 |
| | | 204/266 |
| 2012/0273364 A1 | 11/2012 | Sater |

OTHER PUBLICATIONS

Priya, "Saving Lives: Solar Powered Oxygen Systems Reduce Child Mortality," May 13, 2019, © 2021 Solar Magazine.
Lin et al.,"Emerging opportunities for black phosphorus in energy applications," Materials Today Energy 12 (2019) 1-25.

\* cited by examiner

SOLAR-POWERED OXYGEN PRODUCTION SYSTEM FOR HOSPITALS

BACKGROUND

1. Field

The disclosure of the present patent application relates to oxygen supply systems for hospitals and, particularly, to a solar-powered oxygen production system for hospitals.

2. Description of the Related Art

In hospital settings, oxygen supply can be the difference between life and death. In fact, during the recent COVID pandemic, oxygen supplies in hospitals has become an important issue, as the supply of oxygen sometimes runs low, while patients have an urgent need for oxygen. Generally oxygen is shipped to hospitals and stored in tanks, where it is then distributed to various locations using a pipeline system. Oxygen concentrators and other methods of producing or purifying oxygen, such as electrolysis, are energy intensive. The energy required can be reduced through the use of catalysts and photocatalysts. One recently emerging photocatalyst is black phosphorus, which shows great potential for splitting water into hydrogen and oxygen. Nevertheless, the currently available devices and methods are unable to produce a steady supply of oxygen without expensive and energy-consuming components.

Thus, a solar-powered oxygen production system for hospitals is desired.

SUMMARY

The solar-powered oxygen production system for hospitals includes one or more photovoltaic (PV) solar panels mounted on the roof of a hospital and an oxygen production system housed within the equipment room of the hospital. The solar panels provide the electrical power needed for the oxygen production system. The solar panels are mounted on the roof using solar panel supports that position the solar panels directed at an angle to the horizon that provides the maximum power output from the solar panels. The number of panels and the power output of each panel can be selected depending on the electrical power requirements of the oxygen production system.

The oxygen production system includes an air tank and a photocatalyst tank. The air tank houses atmospheric air, while the photocatalyst tank houses a black phosphorous quantum dot (BPQD) supply. A pipeline system conveys a mixture of atmospheric air from the air tank and BPQDs from the photocatalyst tank to an oxygen production chamber. The oxygen production chamber includes at least one LED for activating the BPQDs, the absorption of photons from light causing electrons and corresponding electron holes to migrate from the valence band to the conduction band at the surface of the photocatalyst. The activated photocatalyst reacts with water vapor present in the atmospheric air, producing hydrogen ions and hydroxyl radicals. The reaction proceeds by two pathways, the hydrogen ions accepting electrons to produce hydrogen molecules (stored in a hydrogen tank), and reaction of two hydroxyl radicals to produce water and elemental oxygen (stored in an unfiltered oxygen tank). The electrical energy from the solar panels may be stored in rechargeable batteries so that oxygen can be produced at night or during other times of reduced sunlight. The unfiltered oxygen from the unfiltered oxygen tank flows through a sterile oxygen filter and an oxygen flow meter, and the filtered oxygen is directed to and stored in one or more medical grade oxygen tanks. The filtered oxygen may also be directed to the hospital oxygen supply where it is directed to the various rooms and other locations through outlets from the hospital oxygen supply.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
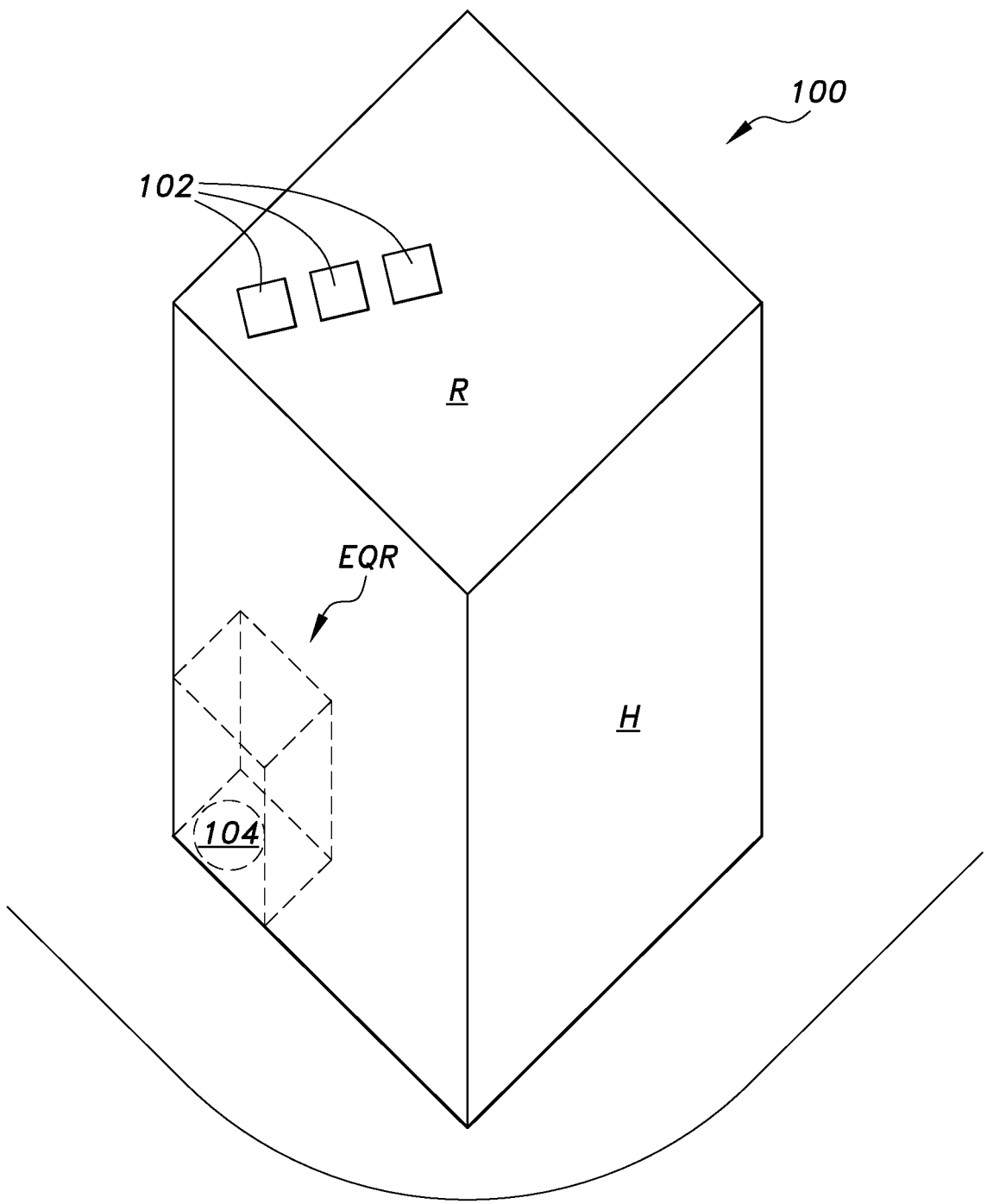
FIG. 1 is a schematic diagram of a hospital having a solar-powered oxygen production system for hospitals installed therein.

A hospital having a solar-powered oxygen production system for hospitals 100 is shown schematically in FIG. 1 having components installed on the roof R and in an equipment room EQR of the hospital H. The solar-powered oxygen production system 100 includes one or more (three shown) photovoltaic (PV) solar panels 102 mounted on the roof R that provide the electrical power needed for an oxygen production system 104 housed within the equipment room EQR.

Figure 2:
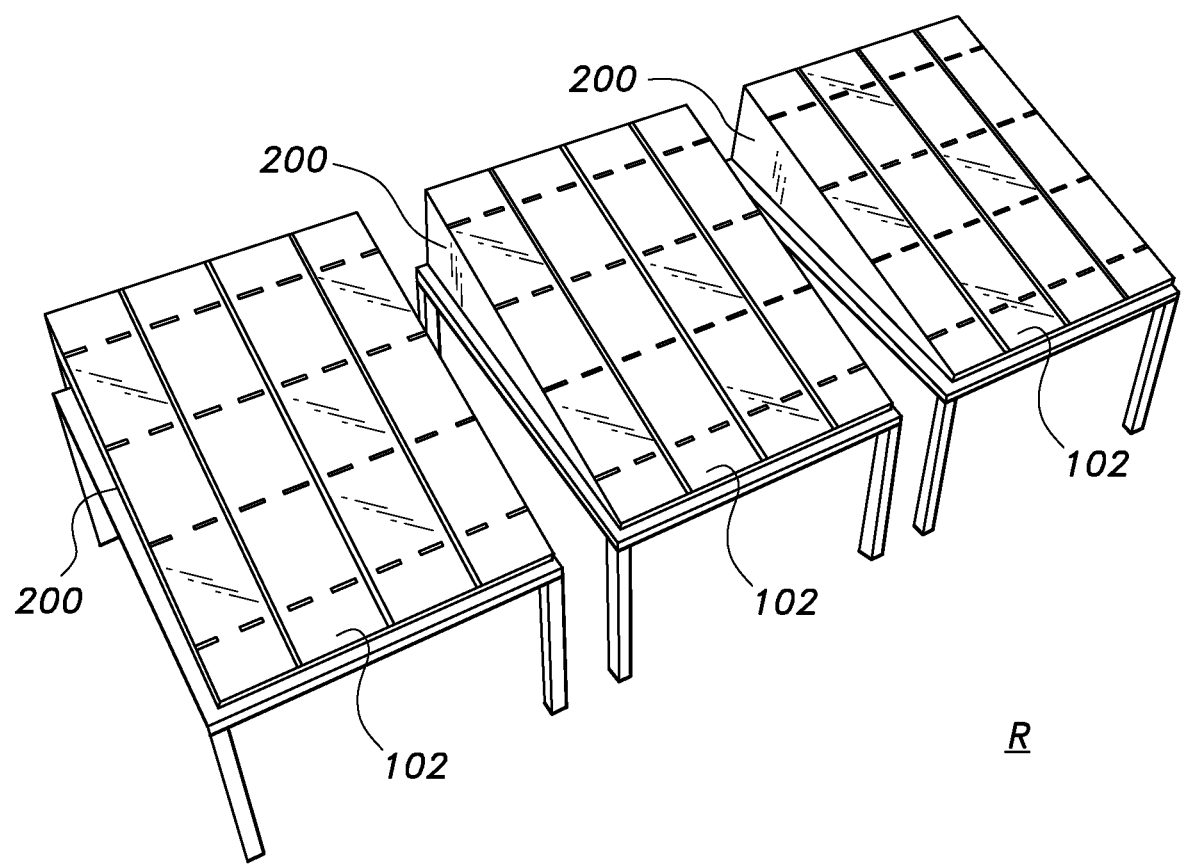
FIG. 2 is a perspective view of a plurality of solar panels in a solar-powered oxygen production system for hospitals.

As shown in FIG. 2, the solar panels 102 may be mounted on the roof R using solar panel supports 200. As is known in the PV solar panel art, the solar panel supports 200 position the solar panels directed south at an angle to the horizon that provides the maximum power output from the solar panels 102. The supports 200 may include tracking mechanisms and software to further maximize the power output from the solar panels 102, such as maximum power point tracking (MPPT), as is known in the PV solar panel art. It should be noted that while three solar panels 102 are shown in FIGS. 1 and 2, the actual number of panels depends on the power output of each panel and the electrical power requirements of the oxygen production system 104.

Figure 3:
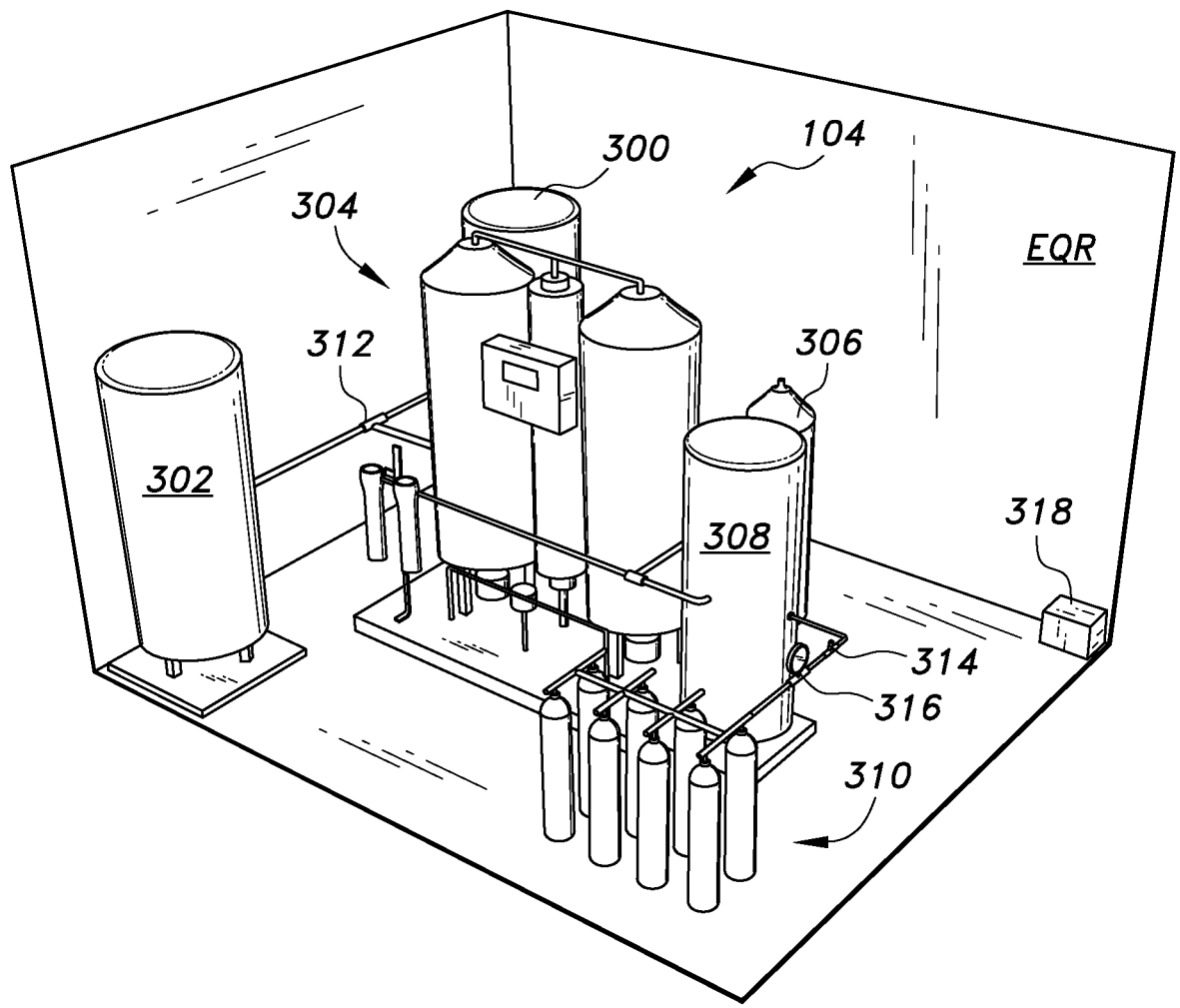
FIG. 3 is a schematic diagram of a possible configuration of the oxygen-generating apparatus of a solar-powered oxygen production system for hospitals.
Figure 4:
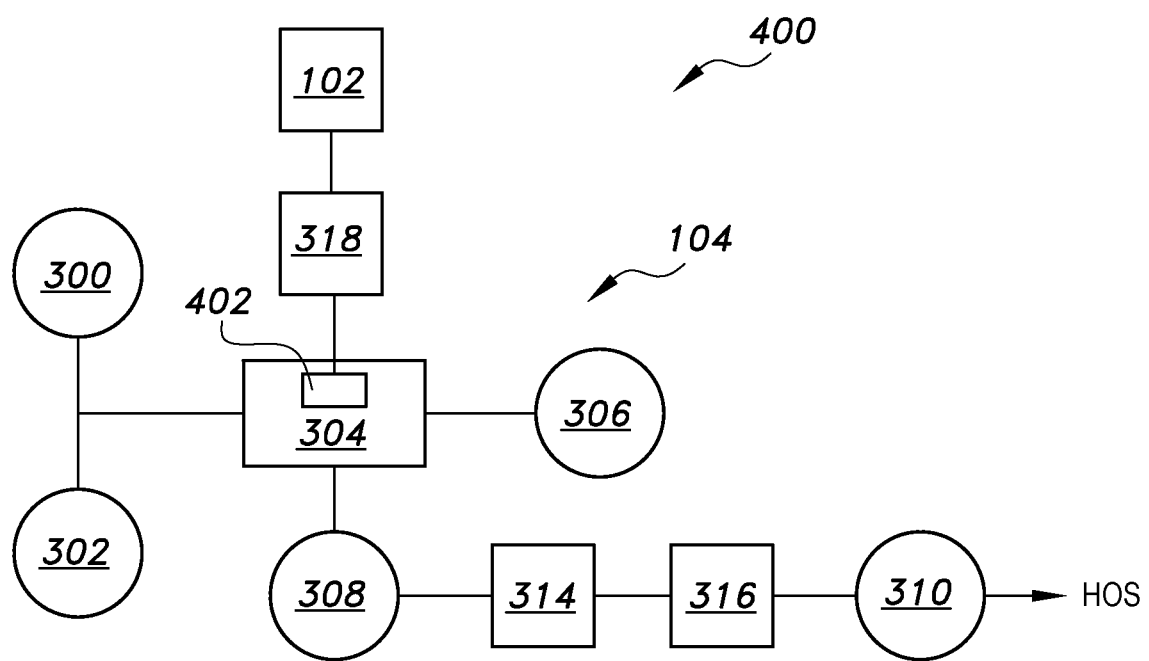
FIG. 4 is a block diagram of a solar-powered oxygen production system for hospitals.

FIG. 3 shows one possible configuration of the oxygen-generating components of the oxygen production system 104 housed within the equipment room EQR, while FIG. 4 is a block diagram 400 of the solar-powered oxygen production system. The oxygen production system 104 includes an air tank 300 and a photocatalyst tank 302. The air tank 300 houses atmospheric air, while the photocatalyst tank 302 houses a BPQDs supply. A pipeline system 312 provides a mixture of air from the air tank 300 and BPQDs from the photocatalyst tank 302 to an oxygen production chamber 304. The oxygen production system 104 further includes a hydrogen tank 306 for receiving hydrogen from the oxygen production chamber 304. Oxygen from the oxygen production chamber 304 is directed to and stored in an unfiltered oxygen tank 308. The unfiltered oxygen from the unfiltered oxygen tank 308 flows through a sterile oxygen filter 314 and an oxygen flow meter 316, and the filtered oxygen is directed to and stored in one or more medical grade oxygen tanks 310. The filtered oxygen may also be directed to the hospital oxygen supply HOS where it is directed to the various rooms and other locations with outlets from the hospital oxygen supply HOS.

The oxygen production chamber 304 includes an LED 402 (shown in FIG. 4) for activating the BPQDs in the water to thereby split the water into hydrogen and oxygen. The electrical energy from the solar panels 102 may be stored in a battery 318 so that oxygen can be produced at night or during other times of reduced sunlight.

While not wishing to be bound by theory, the inventors propose the following mechanism for the production of oxygen in the present system. The possible reaction pathway of the process depends on generating the electron-hole pair on the surface of the proposed photocatalyst of Black phosphorous (BP) without a specific temperature or pressure value. At first, the surface of the designed black phosphorous (BP) is exposed to visible light photons, which are emitted from the sunlight source and/or the LED 402 with equal or greater than their bandgap energy to produce electron-hole pairs. Then, the bandgap value (the difference between the valence band and the conduction band, as known in the semiconductor art) of the black phosphorous photocatalyst will be adjusted to be in the range of 0.3 to 2.0 eV, depending upon the thickness of the designed BP (number of BP layers). This emission will produce a hole in the valence band and an electron in the conduction band. Thus, electron-hole pairs will migrate to the BP surface, then react with adsorbed $O_2$ and vapor $H_2O$ existing in the air. The reaction will proceed in two pathways. The first one produces the hydrogen ion ($H^+$), which goes through a reduction reaction ($2H^+ + 2e^- \rightarrow H_2$) giving hydrogen gas $H_2$ that will be isolated in the hydrogen tank 306. The second pathway produces the photon-generated free radical ·OH that will react with another ·OH radical in order to form a mixture of $H_2O$ and ½ $O_2$ gas (·OH+·OH→$H_2O$+½ $O_2$), then oxygen $O_2$ gas will be isolated and stored in the oxygen tank 308.

It is to be understood that the solar-powered oxygen production system for hospitals is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A solar-powered oxygen production system for hospitals, comprising:
    an atmospheric air source including water vapor;
    a photocatalyst source;
    an oxygen production chamber having an electrical light source;
    a pipeline system for providing a mixture of atmospheric air from the atmospheric air source and photocatalyst from the photocatalyst source to the oxygen production chamber;
    at least one photovoltaic solar panel for supplying electrical energy to the electrical light source;
    an unfiltered oxygen tank for receiving and storing unfiltered oxygen from the oxygen production chamber; and
    a hydrogen tank for receiving hydrogen from the oxygen production chamber,
    wherein the photocatalyst further comprises black phosphorus quantum dots.

2. The solar-powered oxygen production system for hospitals of claim 1, wherein the photocatalyst source comprises a photocatalyst tank containing the black phosphorus quantum dots.

3. The solar-powered oxygen production system for hospitals of claim 2, further comprising at least one battery for storing the electrical energy from the photovoltaic solar panel.

4. The solar-powered oxygen production system for hospitals of claim 1, further comprising:
    at least one medical grade oxygen tank; and
    a sterile oxygen filter, the sterile oxygen tank being disposed in a conduit between the unfiltered oxygen tank and the at least one medical grade oxygen tank for filtering impurities from oxygen generated in the oxygen production chamber before delivery to hospital patients.

5. The solar-powered oxygen production system for hospitals of claim 4, further comprising an oxygen flow meter between the unfiltered oxygen tank and the at least one medical grade oxygen tank.

6. The solar-powered oxygen production system for hospitals of claim 5, wherein the electrical light source is at least one LED.

7. The solar-powered oxygen production system for hospitals of claim 6, wherein the at least one medical grade oxygen tank comprises a plurality of medical grade oxygen tanks.

8. The solar-powered oxygen production system for hospitals of claim 7, wherein the at least one photovoltaic solar panel comprises a plurality of photovoltaic solar panel.

9. A solar-powered oxygen production system for hospitals, comprising:
    an atmospheric air source including water vapor;
    a photocatalyst tank containing black phosphorus quantum dots;
    an oxygen production chamber having at least one LED;
    a pipeline system for providing a mixture of atmospheric air from the atmospheric air source and black phosphorus quantum dots from the photocatalyst tank to the oxygen production chamber;
    a hydrogen tank for receiving hydrogen from the oxygen production chamber;
    an unfiltered oxygen tank for receiving and storing unfiltered oxygen from the oxygen production chamber;
    a plurality of medical grade oxygen tanks;
    a sterile oxygen filter, the unfiltered oxygen from the unfiltered oxygen tank flowing through the sterile oxygen filter and into the plurality of medical grade oxygen tanks;
    an oxygen flow meter between the unfiltered oxygen tank and the plurality of medical grade oxygen tanks;
    a plurality of photovoltaic solar panels for supplying electrical energy to the LED; and
    at least one battery for storing the electrical energy from the photovoltaic solar panel.

10. The solar-powered oxygen production system for hospitals of claim 9, wherein the plurality of photovoltaic solar panels comprises three photovoltaic solar panels.

* * * * *